US006573300B2

(12) United States Patent
Chang et al.

(10) Patent No.: US 6,573,300 B2
(45) Date of Patent: Jun. 3, 2003

(54) HYDROXYUREA TREATMENT FOR SPINAL MUSCULAR ATROPHY

(75) Inventors: Jan-Gowth Chang, Taipei (TW); Yuh-Jyh Jong, Kaohsiung (TW); Fuu-Jen Tsai, Taichung (TW)

(73) Assignee: China Medical College Hospital, Taichung (TW)

( * ) Notice: Subject to any disclaimer, the term of this patent is extended or adjusted under 35 U.S.C. 154(b) by 0 days.

(21) Appl. No.: 09/938,934

(22) Filed: Aug. 24, 2001

(65) Prior Publication Data

US 2003/0040543 A1 Feb. 27, 2003

(51) Int. Cl.$^7$ .............................................. A61K 31/17
(52) U.S. Cl. ....................................................... 514/588
(58) Field of Search ................................. 514/482, 588

(56) References Cited

U.S. PATENT DOCUMENTS

| 6,159,948 A | 12/2000 | Robertson et al. ............. 514/44 |
| 6,245,963 B1 | 6/2001 | Li et al. ........................ 800/9 |

FOREIGN PATENT DOCUMENTS

| EP | 0 167 057 | * 6/1986 |

OTHER PUBLICATIONS

Bergin, A. et al., "Identification and Characterization of a Mouse Homologue of the Spinal Muscular Atrophy–Determining Gene, Survival Motor Neuron", *Gene*, vol. 204, pp. 47–53, 1997.
Burghes, AHM., "When Is a Deletion Not a Deletion? When It Is Converted", *Am. J. Hum. Genet.*, vol. 61:pp. 9–15, 1997.
Burlet, P. et al. "The Distribution of SMN Protein Complex in Human Fetal Tissue and its Alteration in Spinal Muscular Atrophy", *Human Molecular Genetics*, vol. 7, No. 12 pp. 1927–1933, 1998.
Campbell, L et al., "Genomic Variation and Gene Conversion in Spinal Muscular Atrophy: Implications for Disease Process and Clinical Phenotype", *Am. J. Hum. Genet.*, vol. 61, pp. 40–50, 1997.
Chang, JG. et al., "Molecular Analysis of Survival Motor Neuron (SMN) and Neuronal Apoptosis Inhibitory Protein (NAIP) Genes of Spinal Muscular Atrophy Patients and their Parents", *Hum. Genet.*, vol. 100, pp 577–581, 1997.
Coovert, D.D et al., "The Survival Motor Neuron Protein in Spinal Muscular atrophy", *Human Molecular Genetics*, vol. 6, No. 8, pp. 1205–1214, 1997.
Francis, JW. et al., "Heterogeneity of Subcellular Localization and Electriphoretic Mobility of Survival Motor Neuron (SMN) Protein in Mammalian Neural Cells and Tissues", *Proc. Nat. Acad. Sci. USA.*, vol. 95, pp. 6492–6497, 1998.
Gavrilov, DK. et al., "Differential SMN2 Expression Associated with SMA Severity", *Nature genetics*, vol. 20, pp. 230–231, 1998.

Hahnen, E. et al., "Hybrid Survival Motor Neuron Genes in Patients with Autosomal Recessive Spinal Muscular Atrophy: New Insights into Molecular Mechanisms Responsible for the Disease", *Am. J. Hum. Genet.*, vol. 59, pp. 1057–1065, 1996.
Hendrey, J. et al., "Developmental Analysis of the Hba-.sup.th–j Mouse Mutation: Effects on Mouse Peri–Implantation Development and Identification of Two Candidate Genes", *Developmental Biology*, vol. 172, pp. 253–263, 1995.
Hooper, M. et al., HPRT–deficient (Lesch–Nyhan) Mouse Embryos Derived from Germline Colonization by Cultured Cells, *Nature*, vol. 326, pp 292–295, 1987.
Iwahashi, H. et al., "Synergistic Anti–Apoptotic Activity between Bcl–2 and SMN Implicated in Spinal Muscular Atrophy", *Nature*, vol. 390, pp. 413–417, 1997.
Kozbor et al., "The Production of Monoclonal Antibodies from Human Lymphocytes", *Immunology Today*, vol. 4, No. 3, 72–79, 1983.
La Bella, V. et al., "Survival Motor Neuron (SMN) Protein in Rat is Expressed as Different Molecular Forms and is Developmentally Regulated", *European Journal of Neuroscience*, vol. 10, pp. 2913–2923, 1998.
Laemmli, UK., "Cleavage of Structural Proteins during the Assembly of the Head of Bacteriophage T4", *Nature*, vol. 227, pp. 680–682, 1970.
Lefebvre, S. et al., "Correlation between Severity and SMN Protein Level in Spinal Muscular Atrophy", *Nature Genetics* vol. 16, pp. 265–269, 1997.
Lefebvre, S. et al., "The Role of the SMN Gene in Proximal Spinal Muscular Atrophy", *Human Molecular Genetics*, vol. 7, pp. 1531–1536, 1998.
Lefebvre, S. et al., "Identification and Characterization of a Spinal Muscular Atrophy–Determining Gene", *Cell*, vol. 80, pp. 155–165, 1995.
Li, H. et al., "Gsh–1 an Orphan Hox Gene, is Required for Normal Pituitary Development", *The EMBO Journal*, vol. 15, No. 4, pp. 714–724, 1996.
Lorson, CL et al. "SMN Oligomerization Defect Correlates with Spinal Muscular Atrophy Severity", *Nature Genetics*, vol. 19, No. 1, pp. 63–66, 1998.
Melki, J., "Spinal Muscular Atrophy", *Current Opinion in Neurology*, vol. 10, pp. 381–385, 1997.
Monani, UR. et al., "A Single Nucleotide Difference the Alters Splicing Patterns Distinguishes that SMA Gene SMN1 from the Copy Gene SMN2", *Human Molecular Genetics*, vol. 8, No. 7, pp. 1177–1183, 1999.
Parsons, DW. et al, "Intragenic telSMN Mutations: Frequency, Distribution, Evidence of a Founder Effect, and Modification of the Spinal Muscular Atrophy Phenotype by cenSMN Copy Number"., *Am J. Hum. Genet.* vol. 63:1712–1723, 1998.

(List continued on next page.)

*Primary Examiner*—Phyllis G. Spivack
(74) *Attorney, Agent, or Firm*—Fish & Richardson P.C.

(57) ABSTRACT

The invention features a method of modulating SMN exon 7 expression in a subject by administering hydroxyurea to the subject.

11 Claims, 2 Drawing Sheets

OTHER PUBLICATIONS

Pellizzoni, L. et al., "A Novel Function for SMN, the Spinal Muscular Atrophy Disease Gene Product, in Pre–mRNA Splicing", *Cell*, vol. 95, pp. 615–624, 1998.

Pellizzoni, L. et al., "SMN Mutants of Spinal Muscular Atrophy Patients are Defective in Binding to snRNP Proteins", *Proc. Natl. Acad. Sci. USA*, vol. 96, pp. 11167–11172, 1999.

Schreiber, E. et al., "Rapid Detection of Octamer Binding Proteins with 'Mini–Extracts', Prepared from a Small No. of Cells", *Nucleic Acids Research*, vol. 17, No. 15, pp 6419–6419, 1989.

Steege, G. et al., "Apparent Gene Conversions Involving the SMN Gene in the Region of the Spinal Muscular Atrophy Locus on Chromosome 5", *Am. J. Hum. Genet.*, vol. 59, pp 834–838, 1996.

Strasswimmer, J. et al., "Identification of Survival Motor Neuron as a Transcriptional Activator–Binding Protein", *Human Molecular Genetics*, vol. 8, No. 7, pp. 1219–1226, 1999.

Zhang, L. et al., "Whole Genome Amplification from a Single Cell: Implications for Genetic Analysis", *Proc. Natl. Acad. Sci. USA*, vol. 89, pp 5847–5851, 1992.

Fricker, "Mouse model of spinal muscular atrophy," Drug Discovery Today 5:220–221(2000).

Frugier, et al., "Nuclear targeting defect of SMN lacking the C–terminus in a mouse model of spinal muscular atrophy," Human Molecular Genetics 9:849–858 (2000).

Gendron, et al., "Spinal muscular atrophy: molecular pathophysiology," Current Opinion in Neurology 12:137–142 (1999).

Gennarelli et al., "Survival motor neuron gene transcript analysis in muscles from spinal muscular atrophy patients," Biochemical and Biophysical Research 213:342–348 (1995).

Hsieh–Li, et al., "A mouse model for spinal muscular atrophy," Natural Genetics 24:66–70 (2000).

Jong, et al., "Analysis of the mRNA transcripts of the survival motor neuron (SMN) gene in the tissue of an SMA fetus and the peripheral blood mononuclear cells of normals, carriers and SMA patients," Journal of the Neurological Sciences 173:147–153 (2000).

Kijima, et al., "Trapoxin, an antitumor cyclic tetrapeptide, is an irreversible inhibitor of mammalian histone deacetylase*," Journal of Biological Chemistry 268:22429–22435 (1993).

Lorson, et al., "SMN oligomerization defect correlates with spinal muscular atrophy severity," Nature Genetics 19:63–66 (1998).

Lorson, et al., "An exonic enhancer is required for inclusion of an essentioal exon in the SMA–determining gene SMN," Human Molecular Genetics 9:259–265 (2000).

Monani, et al, "The human centromeric survival motor neuron gene (SMN2) rescues embryonic lethality in Smn— mice and results in a muse with spinal muscular atrophy," Human Molecular Genetics 9:333–339 (2000).

Scharf, et al., "Identification of a candidate modifying gene for spinal muscular atrophy by comparative genomics," Nature Genetics 20 (1998).

Wong, et al., "The genetic and molecular mechanisms of motor neuron disease," Current Opinion in Neurobiology 8:791–799 (1998).

Yoshida, et al., "Potent and specific inhibition of mammalian histone deacetylase both in vivo and in vitro by trichostatin A*," Journal of Biological Chemistry 265:17174–17179 (1990).

* cited by examiner

HYDROXYUREA TREATMENT FOR SPINAL MUSCULAR ATROPHY

BACKGROUND OF THE INVENTION

Spinal muscular atrophy (SMA) is an autosomal recessive neurodegenerative disease characterized by degeneration of spinal cord anterior horn cells, which lead to muscular paralysis with muscular atrophy. SMA patients are afflicted to varying degrees of severity and therefore clinically categorized as type 1 (severe), 2 (intermediate), or 3 (mild), according to age of onset and rate of progression. The disorder is found in approximately 1 in 10,000 live births and has a carrier frequency of 1 in 50 (Zerres (1997) *J. Neurol. Sci.* 146:67–72). Type 1 patients have a life expectancy of 18 months or less, whereas type 3 patients can survive into adulthood.

All types of human spinal muscular atrophy are due to mutations in the SMN1 gene of the 5q13 locus on chromosome 5. In most individuals, there exists a second gene, SMN2, adjacent to SMN1. Both SMN1 and SMN2 encode SMN, a 294 amino acid RNA-binding protein (Lefebvre et al. (1995) *Cell* 80:155–165; Monani et al. (1999) *Hum. Mol. Genet.* 8:1177–1183). At the genomic level, only five nucleotides have been found that differentiate the SMN1 gene from the SMN2 gene. Furthermore, the two genes produce identical mRNAs, except for a silent nucleotide change in exon 7, namely, a C→T change six base pairs inside exon 7 in SMN2 as compared to SMN1. This mutation modulates the activity of an exon splicing enhancer (Lorson and Androphy (2000) *Hum. Mol. Genet.* 9:259–265). The result of this and the other nucleotide changes in the intronic and promoter regions is that most SMN2 transcripts lack exons 3, 5, or 7. In contrast, the mRNA transcribed from the SMN1 gene is generally a full-length mRNA with only a small fraction of its transcripts spliced to remove exon 3, 5, or 7 (Gennarelli et al. (1995) *Biochem. Biophys. Res. Commun.* 213:342–348; Jong et al. (2000) *J. Neurol. Sci.* 173:147–153).

Furthermore, there is substantially less transcription of SMN2 than SMN1 in most individuals. As the severity of deletions of the SMN1 indicates, the low level of full-length SMN protein produced by SMN2 is insufficient to protect against spinal muscular atrophy disease (Lefebvre, supra; Coovert et al. (1997) *Hum. Mol. Genet.* 6:1205–1214).

There is no effective treatment to date for spinal muscular atrophy disease.

SUMMARY OF THE INVENTION

The invention is based on the discovery that different classes of compounds have been identified, using new methods, as being useful in the modulation of SMN exon 7 gene expression, and therefore as being useful in the treatment of SMA. It has also been discovered that cells harvested from SMA patients and transgenic animals having particular genotypes and phenotypes are useful in the new screening methods.

Accordingly, the invention features a method for modulating SMN gene expression in a subject. The method includes administering to the subject an amount of hydroxyurea sufficient to increase the expression level of SMN exon 7 in a cell of the subject, relative to a reference expression level of SMN exon 7. For example, the method can increase the ratio of SMN transcripts having exon 7 to those lacking exon 7 by at least 30, 50, 60, 70, 80, 90, 100, or 150%. The cell can be a mammalian cell, e.g., a human cell, e.g., a cell from a human SMA patient. For example, the cell can be homozygous for an SMN1 mutation.

In another aspect, the invention features a method of treating spinal muscular atrophy in a subject. The method includes administering to the subject hydroxyurea in an amount sufficient to ameliorate a symptom of spinal muscular atrophy. The subject can be human, e.g., a human homozygous for mutations in SMN1. The ameliorated symptom can be muscular paralysis, muscular atrophy, breathing, walking gait, or a symptom described herein. The symptom can also be decreased expression of SMN exon 7 in a cell of the subject. The administered amount can be about 0.2 to 100, 0.4 to 80, 5 to 50, or 15 to 25 mg/kg/day. The amount can be administered orally or parentally.

In one embodiment, the subject is a fetus, and the hydroxyurea is administered to the subject in utero.

In still another aspect, the invention features a method of for modulating SMN gene expression in a cell. The method includes contacting an amount of hydroxyurea to the cell. The amount is sufficient to increase the expression level of SMN exon 7 in the cell, relative to a reference expression level of SMN exon 7. The cell can be a human cell, e.g., a cell in a patient. The cell can treated in vivo, in vitro, or ex vivo. Following ex vivo treatment, the cell can be administered (e.g., restored) to a subject, e.g., a human patient.

In yet another aspect, the invention features a method of treating spinal muscular atrophy in a subject. The method includes administering to the subject a DNA replication inhibitor, e.g., a ribonucleotide reductases inhibitor (e.g., hydroxyurea or a compound other than hydroxyurea) in an amount sufficient to ameliorate a symptom of spinal muscular atrophy. The subject can be human, e.g., a human homozygous for mutations in SMN1. The ameliorated symptom can be muscular paralysis, muscular atrophy, breathing, walking gait, or a symptom described herein. The symptom can also be decreased expression of SMN exon 7 in a cell of the subject.

As used herein, the term "transgene" refers to a nucleic acid sequence (e.g., encoding one or more human proteins), which is inserted by artifice into a cell. The transgene is integrated into a chromosomal genome. A transgenic sequence can be partly or entirely species-heterologous, i.e., the transgenic sequence, or a portion thereof, can be from a species which is different from the cell into which it is introduced. A transgenic sequence can be partly or entirely species-homologous, i.e., the transgenic sequence, or a portion thereof, can be from the same species as is the cell into which it is introduced. If a transgenic sequence is homologous (in the sequence sense or in the species-homologous sense) to an endogenous gene of the cell into which it is introduced, then the transgenic sequence has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous gene); it includes a mutation, e.g., a mutation which results in misexpression of the transgenic sequence; by virtue of its insertion, it can result in misexpression of the gene into which it is inserted, e.g., the insertion can result in a knockout of the gene into which it is inserted. A transgene can include one or more transcriptional regulatory sequences and any other nucleic acid sequences, such as introns, that may be necessary for a desired level or pattern of expression of a selected nucleic acid. A transgene can provide an antisense transcript or a sense transcript, e.g., a transcript encoding a protein.

As used herein, the term "transgenic cell" refers to a cell containing a transgene.

As used herein, a "transgenic animal" is a non-human animal in which one or more (e.g., all) of the cells of the animal contain a heterologous nucleic acid introduced by way of human intervention, such as by transgenic techniques known in the art. The transgene can be introduced into the cell directly, indirectly by introduction into a precursor of the cell, or by way of deliberate genetic manipulation, such as by microinjection, transformation, electroporation, lipofection, or infection with a recombinant virus. In one example, where the transgene is introduced indirectly, the transgene is introduced into a cultured cell, and the nucleus of the cultured cell or of a descendant of the cultured cell is microinjected into an enucleated oocyte to produce a nucleated oocyte which develops into an animal.

As used herein, a "disruption" in reference to an endogenous gene refers to any type of mutation that inactivates an endogenous gene, an exon thereof, or the amino acid sequence encoded by the endogenous gene or exon thereof. Consequently, the mutation can be a deletion of the disrupted gene or portion thereof, a mutation that causes inappropriate splicing (including abolishment of splicing), and/or and insertion into the disrupted gene or portion thereof.

In reference to animal models (e.g., a transgenic mouse model) of SMA, a symptom of SMA is selected from: lethality before birth, before postnatal day 10, or before 4 weeks of age; decreased fetal movement; lethargy; loss or depression of muscular reflexes (e.g., areflexia, loss of gag reflex); hand tremors; peripheral neuropathies; large amplitude, prolonged, polyphasic discharges on active muscle contraction as detected by EMG (electromyography); myopathies; muscular weakness (e.g., weakness in the pelvic girdle, arms, facial muscles, instability of walking gait, paralysis of hind limbs, tongue fasciculation, and atrophy); myasthenia; hypertrophied muscle bundles (e.g., pseudohypertrophy of the calves); fat infiltration in muscle bundles; fibrosis in muscle bundles; necrosis in muscle bundles; muscular dystrophies; atrophy of muscle bundles (e.g., in tail, trunk, or limbs); decreased diameter of muscle fibers in the tail, trunk, or limbs; shorter and enlarged tails; chronic necrosis of the tail tip; subcutaneous edema; and reduced furry coat hair;

The skilled artisan can readily determine which of the list of symptoms would apply to a particular animal model. For example, a shortened tail is relevant only to those animals having a tail, and hand tremors are only relevant to those animals having a hand (e.g., a primate.). A symptom for type 1 muscular atrophy in a mouse includes lethality before postnatal day 10, reduced furry coat hair, and a shortened and enlarged tail.

A used herein, the term "modulating" refers to a change in level, either an increase or a decrease. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value is less than 0.05.

As used herein, "full length SMN gene expression" or "expression level of SMN exon 7" refers to a scenario where an SMN gene is transcribed and the resulting transcripts contain exon 7 of an SMN gene. Specifically, it is of no consequence whether the exon 7-containing transcript is transcribed from the human SMN1 gene or from the human SMN2 gene. Transcripts containing SMN exon 7 are translated into the 294 amino acid SMN polypeptide. The amino acid sequence of the 294 amino acid SMN polypeptide is described in GenBank entry "GI:624186." The nucleic acid sequence of SMN exon 7 is the sequence contained between nucleotides about 868 and about 921 of GenBank entry "GI:624185." The identify of the sixth base of exon 7 can be C (cytosine) if the transcript is derived from SMN1 or U (uracil) if the transcript is derived from SMN2. Exon 7 expression can be analyzed in cells in which SMN1 is deleted or mutated. Thus, the relevant SMN exon 7 sequence contains a uracil at position 873 while the remainder of the sequence is as recited from nucleotides about 868 to about 921 of GenBank entry "GI:624185."

As used herein, a "ribonucleotide reductases inhibitor" is a compound that has an IC50 of less than 800 $\mu$M for inhibition of a mammalian ribonucleotide reductases in an in vitro assay. One exemplary in vitro assay is described in U.S. Pat. No. 5,071,835. Further assays are described in Elford et al. (1981) *Adv. Enz. Reg.*, 19, 151 and Cohen (1985) J. Gen. Virol. 66:733.

A "DNA replication inhibitor" is a compound that when contacted to mammalian cells causes at least 80% of the cells to arrest prior to or in S phase after 36 hours. The position of cells in the cell cycle can be determine by fluorescent activated cell sorting.

Other features, objects, and advantages of the invention will be apparent from the description and from the claims.

DETAILED DESCRIPTION

The invention provides a treatment for spinal muscular atrophy. The treatment was identified using a screening method which incorporates two discoveries. First, an agent which increases expression of SMN gene exon 7 in transformed cell lines from SMA patients is indicative of an effective agent for ameliorating SMA symptoms. Second, the efficacy of an agent for treating SMA can be evaluated by administering to a mouse deleted for the murine SMN locus and bearing a human SMN2 transgene. This screening method has identified hydroxyurea as candidate drugs for treatment for SMA.

Compounds Useful for Treating SMA

A useful class of compounds are DNA replication inhibitors, such as hydroxyurea. Hydroxyurea can cause immediate inhibition of DNA synthesis without adverse direct effects on transcription or translation. Hydroxyurea can arrest cells in the G1 phase of the cell cycle or in a pre-S phase (DNA synthesis) phase.

Hydroxyurea is a potent inhibitor of ribonucleotide reductase, which catalyzes the reduction of ribonucleoside diphosphates to their deoxyribonucleoside. Ribonucleotide reductase (RR, EC 1.17.4.1), which reduces ribonucleotides to 2'-deoxyribonucleotides, is essential to de novo DNA synthesis and plays a direct role in regulating DNA replication (Cory (1988) *Adv. Enzyme Regul.* 27:437–455). Class I, the most common form of RR, comprises two different subunits, a larger subunit denoted R1 and a smaller subunit, denoted R2. The active enzyme is a dimer of dimers, denoted $R1_2 R2_2$. Mouse R1 (mR1) and mouse R2 (mR2)

have molecular masses 90 kDa and 45 kDa, respectively. Class I RRs catalyze the reduction of nucleoside diphosphates. The catalytic reaction is believed to involve long-range electron transfer between a tyrosine radical and the substrate site. More complete descriptions of this enzyme may be found in three recent reviews (Stubbe (1990) *Adv Enzymol. Relat. Areas Mol. Biol.* 63:349–419; Sjoberg (1995) *Nucleic Acids and Molecular Biology* 9:192–224). Deoxyribonucleosides are essential substrates for DNA synthesis; in their absence, DNA synthesis is arrested.

Other ribonucleotide reductase inhibitors include guanazole, 3,4-dihydroxybenzo-hydroxamic acid, N,3,4,5-tetrahydroxybenzimidamide HCI, 3,4-dihydroxybenzamidoxime HCI, 5-hydroxy-2-formylpyridine thiosemicarbazones-alpha-(N)-heterocyclic carboxaldehyde thiosemicarbazones, 4-methyl-5-amino-1-formylisoquinoline thiosemicarbazone, N-hydroxy-N'-amino-guanidine (HAG) derivatives, 5-methyl-4-aminoisoquinoline thiosemicarbazone, diaziquone, doxorubicin, 2,3-dihydroxylbenzoyl-dipeptides and 3,4-dihydroxylbenzoyl-dipeptides, iron-complexed 2-acetylpyridine 5-[(2-chloroanilino)-thiocarbonyl]-thiocarbonohydrazone (348U87), iron-complexed 2-acetylpyridine-5-[(dimethylamino)thiocarbonyl]-thiocarbonohydrazone (A1110U), 2'-deoxy-2'-methylenecytidine 5'-diphosphate (MdCDP) and 2'-deoxy-2',2'-difluorocytidine 5'-diphospahte(dFdCDP),2-chloro-9-(2-deoxy-2-fluoro-beta-D-arabinofuranosyl)-adenosine (Cl-F-ara-A), diethyldithiocarbamate (DDC), 2,2'-bipyridyl-6-carbothioamide, phosphonylmethyl ethers of acyclic nucleoside analogs, [e.g., diphosphates of N-(S)-(3-hydroxy-2-phosphonylmethoxypropyl and N-2-phosphonylmethoxyethyl) derivatives of purine and pyrimidine bases], nitrosourea compounds, acylclonucleoside hydroxamic acids (e.g., N-hydroxy-alpha-(2-hydroxyethoxy)-1 (2H)-pyrimidineacetamides 1-3, and 2-acetylpyridine 4-(2-morpholinoethyl)thiosemicarbazone (A723U)).

Hydroxyurea is rapidly absorbed from the gastrointestinal tract after ingestion, and enters the serum within 2 hours. A dosage for hydroxyurea for administration to a subject can be approximately 10 mg/Kg, 20 mg/kg, 30 mg/kg or 50 mg/kg. One skilled in the art can also modulate the dosage and monitor the subject for treatment and for adverse effects such as bone marrow depression, anemia, and nausea.

In addition to a ribonucleotide reductase inhibitor, DNA replication can be inhibited by a variety of other antimetabolites including: folic acid antagonists (e.g., methotrexate and trimetrexate); pyrimidine analogs (e.g., fluorouracil, fluorodeoxyuridine, CB3717, azacitidine, cytarabine, and floxuridine, gemcitabine), purine analogs (e.g., mercaptopurine, 6-Thioguanine, fludarabine, pentostatin); sugar modified analogs (e.g., cytarabine); and adenosine deaminase inhibitors.

In some embodiments, the administered composition includes hydroxyurea and sodium butyrate. The use of sodium butyrate to treat SMA is described in patent application U.S. Ser. No. 09/735,766.

Formulation. A composition containing an effective amount of an inhibitor can be administered to a subject requiring treatment. The composition can be administered parenterally, intravenously, topically, orally, buccally, nasally, rectally, subcutaneously, intramuscularly, or intraperitoneally. In one implementation, the composition can be injected, e.g., into the cerebro-spinal fluid.

The composition of the treatment is formulated to be compatible with the route of administration. The composition can formulated as a tablet, capsule, solution, powder, inhalant, lotion, tincture, troche, suppository, or transdermal patch.

A solution for parenteral, intradermal, or subcutaneous administration can include: a sterile diluent such as water, saline, glycerin, fixed oils, polyethylene glycols, propylene glycol, or other synthetic solvents; an antibacterial agents such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Oral compositions include tablets, capsules, troches, suspensions, and solutions. Such compositions can be fashioned with an inert diluent or an edible carrier. Capsules are made by combining an appropriate diluent with the compound and filling the capsule with the mixture. Common diluents are starches such as powdered cellulose, or sugars such as sucrose, fructose, or mannitol. Tablets are made by wet or dry granulation or by compression. In addition to the desired compound, compositions for tablets can include: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition (see e.g., U.S. Pat. Nos. 5,417,986, 4,675,381, and 4,450,150).

For administration by inhalation, the compounds are delivered in the form of an aerosol spray from pressured container or dispenser which contains a suitable propellant, e.g., a gas. Systemic administration can also be by transmucosal, e.g., with a nasal spray or suppository, or by transdermal means, e.g., as a salve, ointment, gel, or cream. Such modes of administration can use formulations containing detergents, bile salts, and fusidic acid derivatives.

Dosage. An appropriate dosage for treatment must be determined. An effective amount of an inhibitor is the amount or dose which is required to ameliorate a spinal muscular atrophy symptom in a subject. Determination of the amount or dose required to treat an individual subject is routine to one skilled in the art, e.g., a physician, pharmacist, or researcher. First, the toxicity and therapeutic efficacy of the compound, e.g., hydroxyurea, is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, if means are available to deliver the compound to the affected tissue, i.e., the spinal motor neurons and brainstem neurons, while minimizing damage to unaffected tissue.

In formulating a dosage range for use in humans, the effective dose of an inhibitor can be estimated from studies with SMA-like cells and SMA-like transgenic mice. For example, therapeutically effective dosages in cell culture assays are about 5 ng/ml, 50 ng/ml, 500 ng/ml, 5 µg/ml, and 50 µg/ml of inhibitor. A dose can be formulated in an animal in order to achieve a circulating plasma concentration of inhibitor that falls in this range. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample with high performance liquid chromatography or mass spectroscopy.

Alternatively, the dose can be estimated from tests in an animal model, as described below. Alleviation of symptoms is observed when mice receive an inhibitor in their drinking water at doses of about 4 µg/day, 10 µg/day, 20 µg/day, 40 µg/day, 60 µg/day, and 80 µg/day. An appropriate dose for treating human patients is estimated to be approximately 0.4 mg kg$^{-1}$ day$^{-1}$, 1 mg kg$^{-1}$ day$^{-1}$, 2 mg kg$^{-1}$ day$^{-1}$, 4 mg kg$^{-1}$ day$^{-1}$, 60 mg kg$^{-1}$ day$^{-1}$, or approximately 80 mg kg$^{-1}$ day$^{-1}$. Depending on the method of administration, the appropriate dose can vary, e.g., from about 100 µg kg$^{-1}$ day$^{-1}$ to about 500 mg kg$^{-1}$ day$^{-1}$. The dose for a patient can be optimized while the patient is under care of a physician, pharmacist, or researcher. For example, a relatively low dose of hydroxyurea can be administered initially. The patient can be monitored for symptoms and for expression of SMN exon 7 as described below. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

Monitoring. The efficacy of a dose of inhibitor or any other treatment can be determined in a subject. For example, the subject can be monitored for clinical symptoms, e.g., muscular strength, muscle tone, muscular reflexes, gag reflex, ability to walk, and hand steadiness. An EMG (electromyograph) instrument can be used to assess active muscular contractions. For example, untreated subjects can exhibit large amplitude, prolonged, and polyphasic discharges. Subjects can also be directly monitored for affects on the level of SMN exon 7 expression in cells. For example, blood or tissue samples can be obtained from the subject during treatment, and the level of SMN exon 7 expression in cells of the sample can be determined, e.g., by a nucleic acid or polypeptide detection method described below. Alternatively, histopathologic analysis, including in situ nucleic acid hybridization, or in situ antibody staining, can be used to determine SMN exon 7 expression in a tissue sample, using the reagents and methods described herein.

Screening Reagents

Cell Lines. Cell lines are derived from SMA patients. Such cells are termed "SMA cells" herein. The cells are isolated from a variety of sources and tissues. For example, the cells can be isolated from a blood sample or from a biopsy. The cell can be a stem cell, a fibroblast, or a lymphoid cell. The cells can be propagated in culture according to cell type and origin of the cells. The requisite growth factors can be provided in the media. For example, the media can be supplemented with fetal calf serum, a cocktail of purified factors, or an individual growth factor. The cells can be propagated without being immortalized. Alternatively, the cells can immortalized using a virus or a plasmid bearing an oncogene, or a transforming viral protein, e.g., papilloma E6 or E7 protein.

Procedures for isolating and maintaining lymphoid cells lines are well known in the art and can be found in suitable laboratory manuals, for example, Coligan et al. (1999) Sections 7.19.1–7.22.2, *Current Protocols in Immunology* John Wiley & Sons, Inc.

B cells can be immortalized with Epstein-Barr Virus (EBV). EBV virus is obtained from exponentially growing B95-8 cells (ATCC #CRL1612). The B95-8 cells are grown in a 37° C., 5% $CO_2$ humidified incubator for three days. The culture is then centrifuged at 300×g at 4° C. for ten minutes. The supernatant is filtered through a 0.45 µm filter, aliquoted, and stored at –130° C. A heparinized peripheral blood sample is obtained from an SMA patient. The sample is diluted 1:2 with PBS. 12 ml of the diluted sample is underlayed in a 50 ml conical centrifuge tube containing 12 ml of Ficoll-Hypaque. Ficoll-Hypaque can be purchased as Ficoll-Paque (Pharmacia) or made by dissolving 64.0 g Ficoll (molecular weight 400,000), 99.0 g sodium diatrizoate, and 0.7 g sodium chloride in water such that the final volume is 1 L. The Ficoll gradient is centrifuged for 8 minutes at 1500×g at room temperature, or at 2500 rpm for 30 minutes. The buffy coat interface is removed, transferred to a new 50 ml conical tube, and washed twice with PBS. Washes can be performed by adding PBS, centrifuging for 15 minutes at 300×g, and discarding the supernatant. The cell pellet is then resuspended in HBSS (Hanks balanced salt solution), and washed twice. Finally, the cell pellet is resuspended in 2 ml to 5 ml of complete RPMI-10 media. $10^7$ cells in 2.5 ml of complete RPMI-10 are mixed with 2.5 ml of B95-8 culture supernatant containing EBV, incubated for 2 hours at 37° C., and then combined with 5 ml of RPMI-10 with 1 µg/ml cyclosporin A in a tissue culture flask. The flask is incubated for 3 weeks in a humidified 37° C., 5% $CO_2$ incubator. Subsequently, the cells are mixed and split into two new tissue culture flasks with fresh media. After 1 week, the cells can cryopreserved or used for long-term culture by splitting 1:3 in complete RPMI-10 weekly.

Protocols for transforming and transfecting tissue cultures are well known in the art; see for example Sambrook et al. (1989) *Molecular Cloning: A Laboratory Manual*. Cold Spring Harbor Laboratory Press, New York, and other suitable laboratory manuals. To insert a nucleic acid sequence into a cell, two particularly useful methods are electroporation and lipofection. For electroporation, cells can be collected and resuspended in PBS (phosphate-buffered saline) at a concentration of $2 \cdot 10^6$–$5 \cdot 10^6$ cells/ml. A 0.5 ml mixture of cells can be combined with 20–80 µg of linearized, isolated DNA. and placed in a 0.4 cm electrode-gap cuvette (Biorad). A electroporator, e.g., Biorad Gene Pulser, is used to pulse the cells with a 330 volt pulse at 25 mAmp, 1000 µFarad, and infinite resistance. If the DNA construct contains a drug resistance marker, e.g., a neomycin resistance gene, cells can be grown in media with the drug, e.g., G418, present.

For lipofection, 2 µg of linearized, isolated DNA is mixed with LipfectAMINE™ (GibcoBRL) or another liposomal agent. The mixtures is added to 2·10⁵ cells in a 3.5 cm well of a tissue culture plate. After 48 hours, the cells are split, e.g., 1:1000, and, if a selectable marker is present on the introduced DNA, the cells are grown in the presence of the selecting drug. In one implementation, cells are lipofected with a DNA containing the human SMN2 gene, or a fragment thereof. Such DNA can contain additional features, such as a reporter gene fused to exon 7, and/or a selectable marker.

The cells can be grown in sufficient amount to screen an array of test compounds. Alternatively, cells can be used to assess the effectiveness of individual compounds as SMA treatments.

Figure 1A:
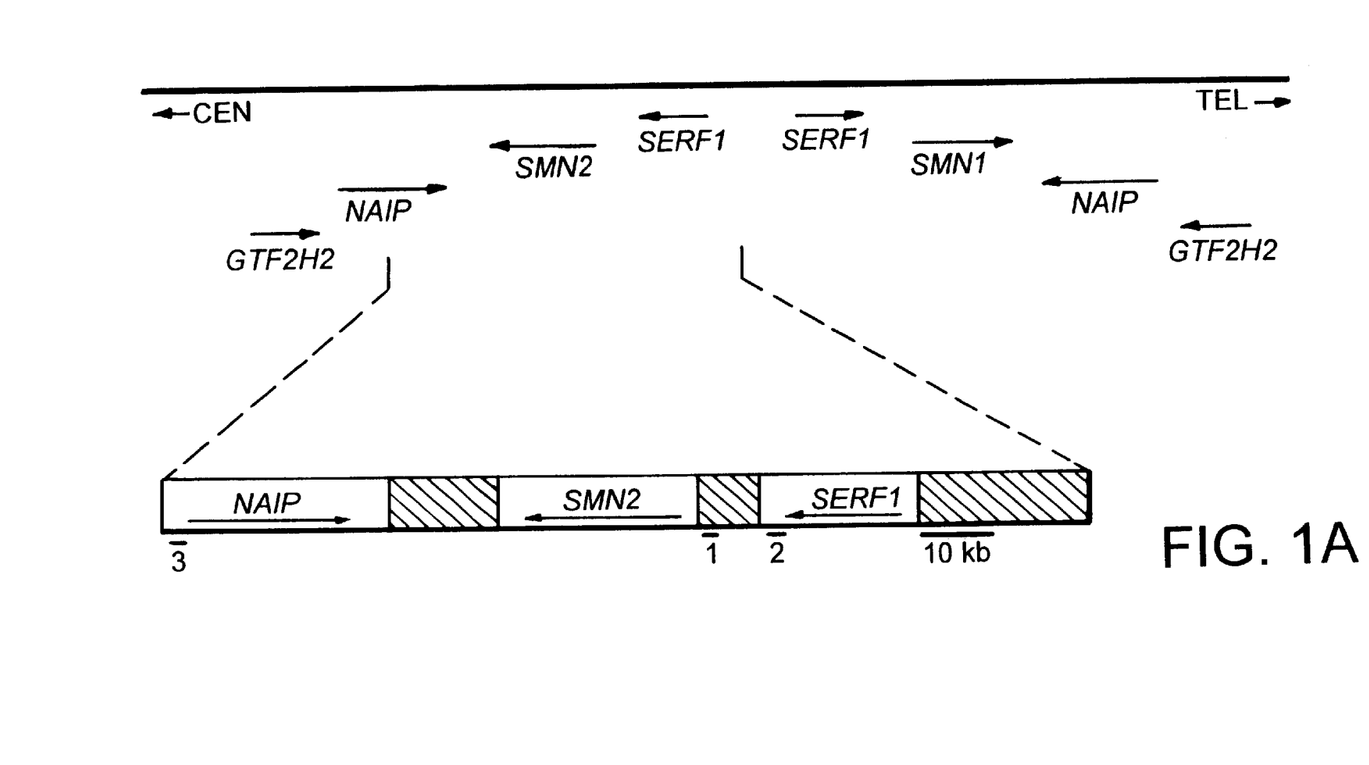
FIG. 1A is a schematic diagram of the human SMN locus used in a method of the invention.

Mice. The generation of transgenic animals is routine in the art. General methods for constructing transgenic mice can be found in Hogan et al. (1994) *Manipulating the Mouse Embryo,* Cold Spring Harbor Laboratory Press, New York. A transgenic mouse bearing the human SMN2 gene is constructed. An isolated nucleic acid containing the human SMN2 gene can be obtained from a YAC, BAC or P1 clone spanning the SMN2 locus. For example, a BAC containing the human SMN2 locus can include about 35 kb, 50 kb, 80 kb, 100 kb, or preferably about 110 kb. Such a BAC can include genes flanking the human SMN2 gene, e.g., SERF1, and NAIP, or fragments thereof (see FIG. 1A). In one example, the human genomic DNA in the BAC is contiguous and identical to human DNA from the 5q13 region of human chromosome 5.

A variety of murine strains, such as FVB/N and C57BL/6, are suitable for use in the invention.

Mouse with a mutated murine SMN locus can be generated using gene targeting. A positive-negative selection vector, e.g., pGGKOV, can be used to target the locus. The invention features a mouse bearing a homozygous disruption of the murine SMN locus and the human SMN2 transgene. Such mice are generated by crossing a transgenic mouse containing the human SMN2 gene (hSMN2) with a mouse which is heterozygous for a disruption in the murine Smn gene, i.e. Smn$^{+/-}$. Among the progeny of the cross is another mouse of this invention, the mouse being heterozygous for a disruption in the murine Smn gene, i.e. Smn$^{+/-}$ and bearing a transgene with hSMN2. Thus, the genotype of the mouse is Smn$^{+/-}$ hSMN2. Since mice lacking a SMN gene, whether endogenous or heterologous, are not viable, the Smn$^{+/-}$ hSMN2 mouse is useful as founder stock for the purposes of this invention.

The Smn$^{+/-}$ hSMN2 mouse can be bred using a F1 intercross, wherein siblings having both the Smn$^{+/-}$ hSMN2 genotype are mated to each other. Alternatively, the Smn$^{+/-}$ hSMN2 mouse can be mated to a Smn$^{+/-}$ mouse lacking hSMN2. The progeny of these crosses include mice which are homozygous for the murine SMN disruption, i.e. Smn$^{-/-}$, and which further contain the hSMN2 gene. These mice exhibit SMA symptoms and are used as an animal model for the human SMA, as described herein.

If these Smn$^{-/-}$ hSMN2 mice (also referred to as "SMA-like mice") are not severely affected, i.e. they show type 3 symptoms, they can be bred and used as founder stock to produce progeny of similar genotype, some of which can be more severely affected.

SMN Exon 7 Expression Analysis

The expression of SMN exon 7 is monitored, for example, in cells treated with a test compound, or in mock-treated cells. Generally, if the mean level of SMN exon 7 expression in cells treated with "test compound" is greater than the mean level of expression from a series of negative control experiments (e.g., mock-treated samples, or a set of inactive test compounds), and if the difference between the means is at least 2.5 times the standard deviation of the series of negative control experiments, then the "test compound" is considered a candidate for treatment of spinal muscular atrophy. Smaller differences in the means, however, are also useful in identifying potential compounds.

A number of techniques for monitoring SMN exon 7 expression are available. The production of transcripts containing exon 7 can be monitored directly. Polypeptides which include peptides encoded by SMN exon 7 can be detected, e.g., with an antibody. Additional methods are available.

Nucleic Acid Detection Assays

A variety of techniques are routinely practiced in the art to qualitatively and quantitatively assess the expression of an exon as an mRNA transcript. Generally, cells are cooled, and rapidly lysed, e.g., with a detergent or phenol. RNA is purified from the lysate, for example, by precipitation, or using a column, e.g., a oligo-dT column for binding polyadenylated RNA, particularly mRNA. The isolated RNA is resuspended in solution, e.g., in water with 10 mM Tris.HCl pH 8.0, 1 mM EDTA. The water can be treated to inactivate or remove possible contaminating nucleases. The isolated cellular RNA is then probed for SMN exon 7, for example using a Northern blot or using reverse transcription and PCR (RT-PCR).

RNA isolation. The isolation of total RNA from mammalian cells is routine in the art (e.g., see Sambrook et al. supra.). Cells are washed with PBS, then lysed with RNA extraction buffer (0.14 M NaCl, 1.5 mM MgCl$_2$, 10 mM Tris.HCl (pH 8.6), 0.5% Nonidet-P40 (NP-40), 1 mM dithiothreitol, Rnasin) and digested with proteinase K at 200 µg/ml. The lysate is sheered by repeated passage through a 21-gauge needle. The lysate is then extracted with phenol:chloroform (1:1), and centrifuged. The aqueous layer is then removed, mixed with 2.5 volumes with ice-cold ethanol for 1 hour at 4° C., then centrifuged. The RNA pellet is washed and resuspended for further analysis.

Northern Blotting. Isolated RNA, about 2–10 µg/lane is electrophoresed on an agarose gel, e.g., a 1.2% agarose gel containing 6.5% formamide and 20 mM MOPS (pH 7.0) 8 mM sodium acetate, 1 mM EDTA. The gel is electrophoresed at 120 V for approximately 2 hours or until adequate separation is achieved. The gel is then placed on a nitrocellulose filter and blotted overnight using 2×SSC (17.3 g sodium chloride, 8.82 g sodium citrate pH 7.0 per 1 L) and a wick made of Whatman 3MM paper. After blotting, the filter is rinsed and crosslinked with ultra-violet light. The filter is then mixed with a radiolabeled SMN exon 7 probe. The probe can be produced from isolated SMN exon 7 nucleic acid which is hybridized with random primers, and incubated with Klenow DNA polymerase, $^{32}$P-dATP, dCTP, dGTP, and dTTP. Alternatively, the probe can be produced by PCR using appropriate primers and $^{32}$P-dATP. The probe is then denatured and combined with the filter in hybridization buffer consisting of 18% formamide, 5×SSC, 5×Denhardt's Solution, 1% SDS, and 100 µg/ml denatured salmon sperm DNA. After 8–18 hours of incubation at 42°

C., the hybridization buffer is removed, and the filter is washed two to three times at 65° C. with 2×SSC. The filter is then dried and autoradiographed. mRNAs containing exon 7 appear as bands on the autoradiogram.

RT-PCR. Isolated RNA can be reverse transcribed using a primer, e.g., random primers, and MMLV reverse transcriptase (Promega). This reaction produces single-stranded cDNA which can be amplified by the polymerase chain reaction (PCR) using a thermostable DNA polymerase, and a pair of primers covering the SMN exon 7. One of the primers flanks exon 7 on the 5' end, the other flanks exon 7 on the 3' end. For example, one primer can anneal to coding sequences in exon 6, the other in exon 8. Alternatively, one or both of the primers can anneal to coding sequences in exon 7 itself. The amplification product is detected by agarose gel electrophoresis, ethidium staining, and illumination under a UV-light source. The amplification of exon 7 nucleic acid is indicative of exon 7 expression.

TaqMan assay. A real-time PCR assay can be used to sensitively detect exon 7 transcripts using TaqMan technology and a Perkin-Elmer ABI7700 Sequence Detection system. After reverse transcription of a sample, the sample is prepared for a standard PCR reaction with oligonucleotides that will prime synthesis of fragment containing exon 7 nucleic acid or a fragment thereof. A third oligonucleotide, which is covalently linked to fluorescent dyes at its 3' and 5' ends, and which hybridizes to exon 7 is added. A fluorescent dye, such as 6-FAM, is used at the 5' end while a dye which quenches the 5' moiety is used at the 3' end, such as TAMRA. As a result of the quenching, prior to use the fluorescent signal is low. However, if exon 7 sequences are present, the labeled oligonucleotide is utilized. The nucleolytic activity of Taq polymerase removes the 3' quenching dye and allows the remaining 5' dye to fluoresce. Thus, the PCR cycle when fluorescence is first detected is proportional to the concentration of template. The amount of total RNA can be internally controlled with a second oligonucleotide set which includes a probe oligonucleotide with a different fluorophore to a control mRNA, such as actin.

Other molecular techniques can be used to detect the exon 7-containing SMN mRNA species. In one case, the ligase chain reaction is employed. In another case, hybridization to a microarray is monitored. The microarray, see below, can include additional nucleic acids to detect other transcripts whose splicing can be affected by treatment.

Antibody Assays

Alternatively, SMN exon 7 expression is monitored with an antibody specific to a polypeptide containing amino acids encoded by exon 7. The generation of specific antibodies is routine in the art.

For example, antibodies are generated to human SMN exon 7 as follows. Oligonucleotide primers are designed to amplify exon 7 nucleic acid such that the sequences are flanked by a restriction site, that is compatible with a protein expression vector. Many protein expression vectors are commercially available for overproducing proteins in bacteria, insect cells, yeast, and mammalian cells. In one implementation, a vector containing the glutathione-S-transferase (GST) gene is used (Pharmacia). The vector includes unique restriction sites for in-frame fusion with GST. The PCR amplification product is cloned in-frame into the vector and transformed into an E. coli host cell. After protein synthesis is induced, the cells are harvested and lysed. The GST fusion to SMN exon 7 is purified on glutathione-coupled agarose beads, and eluted with free glutathione. Alternatively, the antigen can be removed from the column by cleavage with a specific protease, e.g., thrombin or factor Xa, provided that the requisite protease cleavage site was encoded in the linker between the GST gene and the inserted gene, i.e. SMN exon 7. If necessary, the antigen can be further purified, e.g., using ion-exchange chromatography, or by polyacrylamide gel electrophoresis. In the latter case, the antigen can be electroeluted from excised gel bands. The purified antigen is used to immunize rabbits, mice, hamsters, guinea pigs, or rats. An adjuvant can be used to enhance the immune response to the antigen. Adjuvants that can be used include Freund's (complete and incomplete), mineral gels, e.g., aluminum hydroxide, surface active substances, e.g., lysolecithin, pluronic polyols, polyanions, peptides, oil emulsions, keyhole limpet hemocyanin (KLH), and adjuvants compatible with use in humans, e.g., BCG (bacille Calmette-Guerin) and *Corynebacterium parvum*.

Monoclonals antibodies produced from a hybridoma cell are of utility as the hybridoma provides a homogenous population or antibodies. Hybridomas can be produced by fusing lymphoid cells from the spleen of immunized mice with an appropriate myeloma cell to produce a hybridoma (see, e.g., Kohler et al. (1975) *Nature* 256:495; Kohler et al., (1976) *Eur. J. Immunol.* 6:292; Hammerling et al., (1981) In *Monoclonal Antibodies and T Cell Hybridomas,* Elsevier, N.Y.; U.S. Pat. No. 4,376,110; Kosbor et al. (1983) *Immunology Today* 4:72; Cole et al., (1983) *Proc Natl Acad Sci USA* 80:2026; Cole et al. (1983) *Monoclonal Antibodies and Cancer Therapy,* Alan R. Liss, Inc., pp. 77–96) Monoclonal antibodies can be of any immunoglobulin class, e.g., IgG, IgM, IgE, IgA, or IgD, and of any subclass thereof. The hybridoma producing the monoclonal antibody can be cultivated in vitro or in vivo, e.g., in a mouse to obtain ascites fluid.

Antibodies are purified on beads coupled with the antigen and/or with Protein A-agarose. Antibodies can be tested for affinity and specificity by their ability to selectively recognize the antigen in a crude lysate by Western blot analysis or immunoprecipitation. Methods for Western blotting and immunoprecipitation are routine in the art and are described in Ausubel et al. (1994) *Current Protocols in Molecular Biology,* John Wiley & Sons, NY. Antibodies can be further modified to generate Fab fragments, $F(ab')_2$ fragments, humanized antibodies, chimeric antibodies, and single chain antibodies.

In an alternative example, peptides containing sequences from SMN exon 7 are synthesized. The peptides are coupled to a carrier protein, e.g., KLH protein, and used to immunize animals as described above.

The SMN exon 7-specific antibodies are used to measure expression of exon 7 in SMA cells or in tissue samples and/or sections from patients and mice. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, and $^{3}H$.

To detect SMN exon 7 expression in cells, lysates can be prepared. Cells can be lysed in 25 mM Tris.HCl (pH 7.5), 50 mM potassium chloride, 1 mM dithiothreitol, 0.1% NP-40, 0.5 mM PMSF. Clarified lysates can either be analyzed by gel electrophoresis and Western blotting, or can be used to coat a plastic plate, and analyzed by ELISA (enzyme-linked substrate assay).

Reporter Gene Assays

In another implementation, a reporter gene is utilized to monitor the splicing of SMN2 exon 7. In a nucleic acid construction, the reporter gene is fused in frame to the SMN2 exon 7 in a region that itself is not required for splicing regulation. The construction also includes the remainder of the SMN2 gene such that the alternative splicing predilections of the SMN2 gene are recapitulated by the reporter. Alternatively, one skilled in the art can reduce the construction to smaller regions of the SMN2 gene such that the reduced region with the inserted reporter recapitulates the alternative splicing preferences of exon 7. Hydroxyurea is a useful positive controls for assessing the veracity of a reporter construct. The nucleic acid construction is transformed into SMA cells, e.g., by a transfection protocol or lipofection to generate SMA reporter cells.

In one implementation, the reporter gene is green fluorescent protein. In a second implementation, the reporter is β-galactosidase. In still other implementations, the reporter gene is alkaline phosphatase, β-lactamase, luciferase, or chloramphenicol acetyltransferase. The nucleic acid construction can be maintained on an episome or inserted into a chromosome, for example using targeted homologous recombination as described in Chappel, U.S. Pat. No. 5,272,071 and WO 91/06667.

In the implementation utilizing green fluorescent protein (GFP) or enhanced GFP (eGFP) (Clontech, Palo Alto, Calif.), the SMA reporter cells are grown in microtiter plates wherein each well is contacted with a unique agent to be tested. Following a desired treatment duration, e.g., 5 hours, 10 hours, 20 hours, 40 hours, or 80 hours, the microtiter plate is scanned under a microscope using UV lamp emitting light at 488 nm. A CCD camera and filters set to detect light at 509 nm is used to monitor the fluorescence of GFP, the detected fluorescence being proportional to the amount of reporter produced as a consequence of altered splicing that favors exon 7 inclusion.

In the implementation utilizing β-galactosidase, a substrate which produces a luminescent product in a reaction catalyzed by β-galactosidase is used. Again SMA reporter cells are grown in microtiter plates and contacted with compounds for testing. Following treatment, cells are lysed in the well using a detergent buffer and exposed to the substrate. Lysis and substrate addition is achieved in a single step by adding a buffer which contains a 1:40 dilution of Galacton-Star™ substrate (3-chloro-5-(4-methoxyspiro{1,2-dioxetane-3,2'-(4'chloro)-tricyclo-[3.3.1.1$^{3,7}$]decan}-4-yl)phenyl-B-D-galactopyranoside; Tropix, Inc., Cat.#GS100), a 1:5 dilution of Sapphire II™ luminescence signal enhancer (Tropix, Inc., Cat.#LAX250), 0.03% sodium deoxycholic acid, 0.053% CTAB, 250 mM NaCl, 300 mM HEPES, pH 7.5). The cells are incubated in the mixture at room temperature for approximately 2 hours prior to quantitation. β-galactosidase activity is monitored by the chemiluminescence produced by the product of β-galactosidase hydrolysis of the Galacton-Star™ substrate. A microplate reader fitted with a sensor is used to quantitate the light signal. Standard software, for example, Spotfire Pro version 4.0 data analysis software, is utilized to analyze the results. The mean chemiluminescent signal for untreated cells is determined. Compounds which exhibit a signal at least 2.5 standard deviations above the mean are candidates for further analysis and testing. Similarly, for alkaline phosphatase, β-lactamase, and luciferase, substrates are available which are fluorescent when converted to product by enzyme.

Microarrays. A large-scale or genome-wide analysis can identify additional transcripts which are either over- or under-expressed in SMA cells. For example, the splicing of other genes may be affected by a compound which affects SMN exon 7 splicing. Notably, the SMN protein itself is involved in mRNA splicing. Therefore, the production of full length SMN protein may impact the splicing of other genes. Alternatively, the compound may directly affect the splicing of other genes by the same mechanism as it affects SMN gene splicing.

Regardless, other affected transcripts can be identified by standard microarray experiments. A microarray can comprise a two-dimensional substrate having a plurality of addresses, with each address being positionally identifiable and having a unique nucleic acid sequence attached. cDNA can be prepared from untreated SMA cells and treated SMA cells. The cDNA is labeled, e.g., with a fluorescent probe, and hybridized to a microarray containing a large number of exonic sequences at addressable locations. The hybridization pattern of cDNA from treated and untreated cells is compared and exons whose levels are altered by treatment are identified. Affected exons can be used as probes in subsequent drug screens. Alternatively, by identifying the gene containing the exon, reporter constructs can be designed to monitor the splicing of affected exons.

Screening a Test Compound

The invention provides methods (also referred to herein as "screening assays") for identifying modulators of SMN exon 7 expression. A "test compound" can be any chemical compound, for example, a small organic molecule, a carbohydrate, a lipid, an amino acid, a polypeptide, a nucleoside, a nucleic acid, or a peptide nucleic acid. The test compound or compounds can be naturally occurring, synthetic, or both. A test compound can be the only substance assayed by the method described herein. Alternatively, a collection of test compounds can be assayed either consecutively or concurrently by the methods described herein.

Such modulators can include macromolecules and small molecules, such as molecules having a formula weight of less than about 10,000 grams per mole, less than 5,000 grams per mole, less than 1,000 grams per mole, or less than about 500 grams per mole. Macromolecules include, but are not limited to polypeptides, e.g., proteins, protein complexes, and glycoproteins, nucleic acids, e.g., DNA, RNA and PNA. (peptide nucleic acid). Small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds). Modulators can be identified using a drug screen. Molecules can be screened individually or in parallel. Compounds can be obtained from a commercial chemical supplier, e.g., Sigma-Aldrich Corp., St. Louis Mo.

An large scale example of the latter is a high throughput drug screen. A high-throughput method can be used to screen large libraries of chemicals. Such libraries of candidate compounds can be generated or purchased e.g., from Chembridge Corp., San Diego, Calif. Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. Alternatively, prior experimentation and anecdotal evidence, can suggest a class or category of compounds of enhanced potential. A library can be designed and synthesized to cover such a class of chemicals.

High Throughput Screening

Transformed cells from SMA patients can be used for high throughput drug screening. For example, the cells can be grown in small microtiter plates, e.g., 6-well, 32-well, 64-well, 96-well, 384-well plates. High density microtiter plates can be fashioned from a polymer, e.g., polydimethylsiloxane, (e.g., Sylgard 384 from Dow-Corning) and an acrylic mold. The mold contains wells for the growth of cells into which compounds can be dispensed. For example, a mold can contain 1536 wells with a 2 $\mu$l capacity, or 6144 wells with a 250 nl capacity. The transformed SMA cells are grown in each well. Then a plurality of candidate compounds can be screened. Alternatively, a library, as described above, can be screened. The library can be provided in a format that is amenable for robotic manipulation, e.g., in microtiter plates. Compounds can be added to SMA cells in microtiter plates. Following compound addition, cells are incubated for a specific time. Then, the expression level of SMN exon 7 is monitored. A high through put screen is further facilitated by the use of a reporter gene to monitor the splicing of SMN2 exon 7 as described above.

The compounds can also be pooled, and the pools tested. Positive pools are split for subsequent analysis. Regardless of the method, compounds which increase the expression level of SMN exon 7 are considered "candidate" compounds or drugs. Candidate compounds are retested on SMA cells as described above. They are also tested on SMA-like mice, as described herein. Candidate compounds that are positive in a retest are considered "lead" compounds.

Optimization of a Compound

Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above described assays can be delineated by examination of structure-activity relationships (SAR) as is commonly practiced in the art. A person of ordinary skill in chemistry could modify moieties on a lead compound and measure the effects of the modification on the efficacy of the compound to thereby produce derivatives with increased potency. For an example, see Nagarajan et al. (1988) *J. Antibiot.* 41:1430–8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., Molecular Simulations, Inc.)

Without further elaboration, it is believed that the above description allows the skilled artisan to practice the present invention. The following examples are, therefore to be construed as merely illustrative, and not limitative of the remainder of the disclosure in any way whatsoever. All of the publications cited herein are hereby incorporated by reference in their entirety.

EXAMPLES

1. Drug Screens for SMN Exon 7 Expression in Cell Lines

To identify drugs for treating spinal muscular atrophy, EBV transformed lymphoid cell lines of all three types of SMA patients were developed and assayed as follows.

Transformed Cell Lines. Lymphoid cells were isolated from SMA patients with different degrees of severity. Whole blood was drawn from the patients, heparinized, then diluted 1:1 with PBS (phosphate buffered saline). The diluted sample was layered on a Ficoll-Hypaque gradient, and centrifuge at 2500 rpm for 30 minutes at room temperature. The buffy coat was collected from the centrifuged sample, washed twice with 5 ml PBS, collected, and resuspended in 5 ml RPMI medium, 0.5 ml Epstein-Barr virus (EBV), 50 $\mu$l PHA, and 50 $\mu$l of cyclosporine (0.2 mg/ml). The virus-treated sample was mixed well and transferred into a T-flask for incubation at 37° C. in a 5% $CO_2$ incubator for 3 weeks.

Several drugs were screened for their ability to increase exon 7 expression from the SMN2 gene. Two types of screens are described, one utilizes RT-PCR analysis, the other an antibody specific to SMN exon 7 epitopes.

RT-PCR analysis. Total RNA from treated lymphoid cells and untreated controls was reverse transcribed using the random primer 5'-$TN_{10}$-3' and MMLV reverse transcriptase (Promega). The resulting single-stranded cDNA was amplified by the polymerase chain reaction (PCR) using one of three pairs of primers covering the entire SMN coding region. The primer pair for amplification of the nucleic acid fragment from the 5' untranslated region to exon 4 was: 5'-CGCTGCGCATCCGCGGGTTTGCTATG GC-3' (forward primer, P1, SEQ ID NO:1) and, 5'-TCCCAGTCTTGGCCCTGGCAT-3' (reverse primer, P2, SEQ ID NO:2). The primer pair for amplification of the nucleic acid fragment from exon 4 to exon 6 was: 5'-AACATCAAGCCCAAATCTGC-3' (forward primer, P3, SEQ ID NO:3), and 5'-GCCAGTATGATAGCCACTCATGTACCATG-3' (reverse primer, P4, SEQ ID NO:4). The primer pair for amplification of the nucleic acid fragment from exon 6 to exon 8 was: 5'-CTCCCATATGTCCAGATTCTCTTGATGA TGC-3' (forward primer, P5, SEQ ID NO:5), and 5'-ACTGCCTCACCACCGTGCTGG-3' (reverse primer, P6, SEQ ID NO:6). Primers P1 and P6 were used to amplify the full length SMN cDNA. PCR amplification products were analyzed on agarose gels. The production of a 419 basepair band from primers P5 and P6 was indicative of increased exon 7 expression, whereas a 365 basepair band was indicative of a splice pattern which excludes exon 7.

Western-blot analysis. Rabbits were immunized with synthetic peptides containing either human SMN amino acids 279–288 from exon 7 or amino acids 72–84 from exon 2. Specific antibodies (H7 and H2 respectively) were purified from rabbit crude sera with an EAH-sepharose 4B column (Pharmacia) according to the manufacturer's instructions.

Protein samples, prepared from treated and untreated SMA lymphoid cells, were loaded on a 5% polyacrylamide stacking gel above a 12% separating gel, and the gel was run with a discontinuous buffer using Laemmli's method. After electrophoresis, proteins were transferred electrophoretically to polyvinyl difluoride membranes (Millipore Corp., Marlborough, Mass., USA). After the transfer, the membranes were blocked in TBST (50 mM Tris.HCl, pH 7.5, 150 mM NaCl, 0.05% Tween 20) containing 4% BSA (bovine serum albumin) for 2 hours at room temperature. Blots were incubated with a 1:800 dilution of anti-SMN exon 2 (H2) or anti-SMN exon 7 (H7) antibody in TBST for 2 hours at room temperature. The blots were washed for three 20-minute periods in TBST and then incubated with a 1:32,000 dilution of an anti-rabbit IgG alkaline phosphatase conjugate (Sigma) in TBST for 1 hour at room temperature. The secondary antibody was detected with a 1.5% solution of 5-bromo-4-chloro-3-indoyl phosphate and 3% nitro blue tetrazolium in a developing buffer (100 mM NaCl, 5 mM $MgCl_2$, 100 mM Tris.HCl, pH 9.5).

2. Effects of Hydroxyurea on SMA-like Cell Lines

One of the compounds, hydroxyurea, changed the expression pattern of exon 7 of the SMN2 gene. The amount of exon 7-containing SMN mRNA increased in the lymphoid cells cultured with 500 ng/ml to 500 μg/ml of hydroxyurea, with the greatest increase being 3 hours after addition of the drug. Moreover, lymphoid cells from all three types of SMA patients showed increased levels of full-length SMN transcript. Since at least one of these cell types contains a deletion of the SMN1 gene, the increase in SMN exon 7 was necessarily due to alterations in SMN2 splicing.

The RT-PCR method described above was used to determine the alternative splice pattern of the SMN2 gene. In untreated cells, SMN2 was spliced to remove exon 7. However, after hydroxyurea treatment, the splicing of SMN2 transcripts was changed to include exon 7 as in the splicing of SMN1 transcripts. Treatment also resulted in an increase in the amount of full-length SMN mRNA transcript, relative to the untreated control. The alternative splicing patterns of exons 3 and 5 were unchanged.

In addition, hydroxyurea treatment resulted in an increase in the levels of exon 7-containing SMN protein. Lymphoid cell lines established from different types of SMA patients were treated with varying amounts of hydroxyurea and compared to untreated controls. Western blot analysis using the H2 and H7 antibodies produced as described above indicated that hydroxyurea increase the amount of intact SMN protein. This increase in intact SMN protein was evident in both cytosolic and nuclear fractions after 3 hours stimulation with 5 ng/ml to 500 μg/ml of hydroxyurea.

3. Generation of Mice with SMA-like Symptoms

Figure 1B:
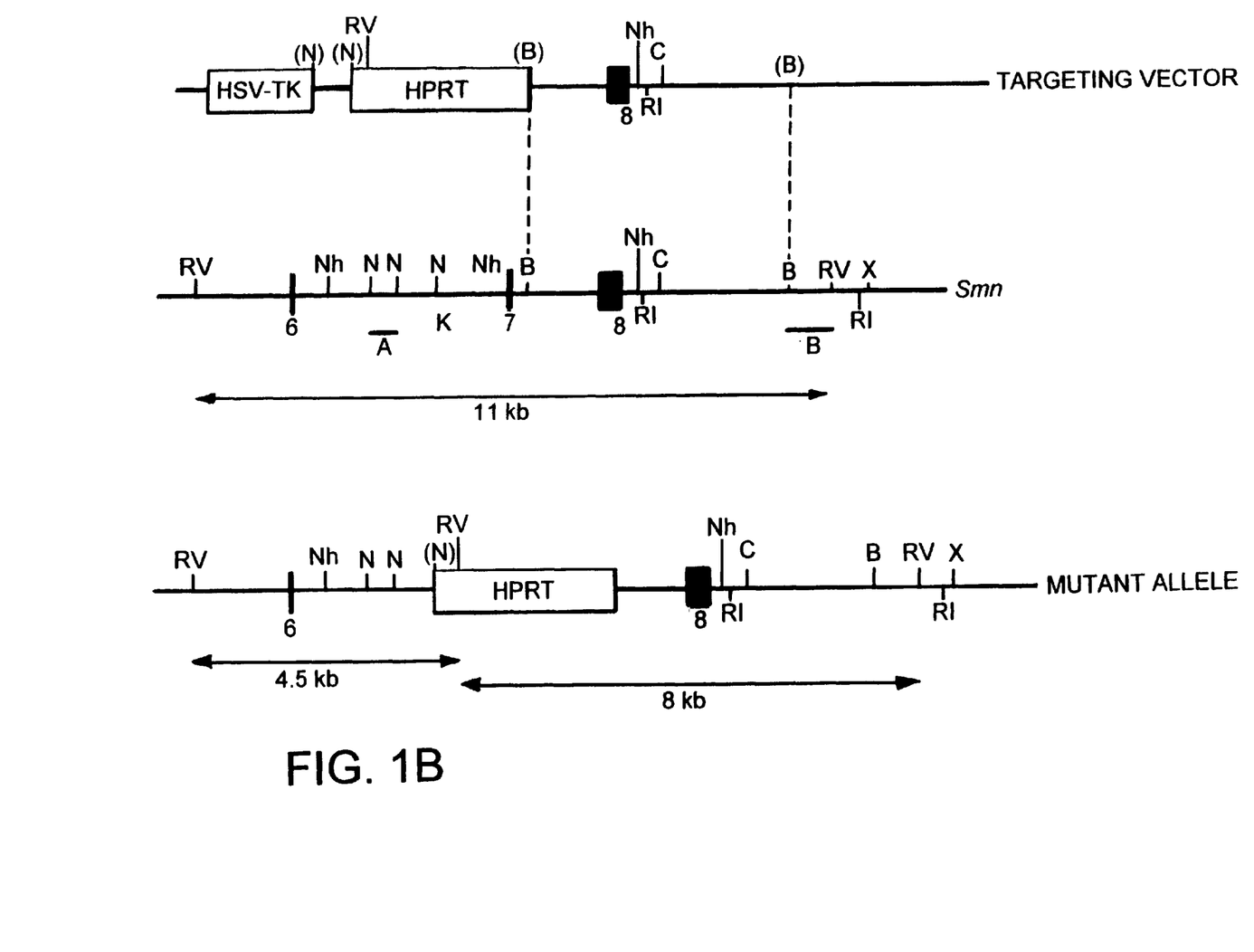
FIG. 1B is a schematic diagram of the mouse SMN locus and an insertion of human sequences into the mouse locus in a method of the invention.

Transgenic Mice. A mouse containing a mutation in the murine SMN gene was generated with the plasmid pGGKOV-SMN (Hsieh-Li et al. (2000) *Nature Gen.* 24:66–70). This plasmid contains a 1.6 kb deletion of the murine SMN locus. The deletion removes exon 7. To generate pGGKOV-Smn, the 4.6 kb BamHI fragment and the 0.6 kb NdeI fragment of the mouse genomic clone MSG24-4, which spans the SMN cDNA exons 2 to 8, were cloned into the BamHI and ClaI sites, respectively, of the pGKKOV vector (see FIG. 1B). For details of the pGGKOV vector and methods for its use see Li et al. (1996) *EMBO J.* 115:714–724.

pGGKOV-Smn was linearized with NotI and electroporated into E14TG2a embryonic stem cells. Cells were selected for integration of the HPRT gene and against integration of HSV-thymidine kinase, in order to obtain homologous recombinants which disrupt the Smn exon 7 as described (Li et al., supra). Cells were injected into C57BL/6 blastocysts using standard procedures (Hogan et al., supra). The resulting mice were bred and individuals heterozygous for the Smn gene disruption were identified by genotyping.

hSMN2 transgenic mice were generated as follows. The 115 kb insert of the hSMN2 BAC clone 7C was excised with NotI, purified on an agarose gel, and electroeluted from the gel. The 115 kb insert includes, from the centromeric side to the telomeric side, the NAIP gene, the SMN2 gene, the SERF1 gene, and 35 kb of nucleic acid telomeric to the SERF1 gene (see FIG. 1A). The DNA was then diluted to 2 ng/μl and injected into FVB/N male mice pronuclei as described (Hogan et al., supra).

To generate hSMN2 $Smn^{+/-}$ mice, a mouse heterozygous for the murine Smn disruption was crossed to a mouse containing the hSMN2 transgene. Progeny were genotyped to identify hSMN2 $Smn^{+/-}$ mice.

To generate hSMN2 $Smn^{-/-}$ mice, hSMN2 $Smn^{+/-}$ mice were crossed to $Smn^{+/-}$ mice. Progeny lacking the murine SMN locus were identified by genotyping. The presence of the hSMN2 transgene was also confirmed. Such mice, having the hSMN2 $Smn^{-/-}$ genotype, exhibit a range of SMA symptoms and are referred to as "SMA-like" mice.

Mice with the most severe pathology (type 1) did not develop furry hair and died before postnatal day 10. Mice with intermediate severity (type 2) were inactive, and died at approximately 2 to 4 weeks. These mice frequently developed chronic necrosis of the tail tip, muscular atrophy, subcutaneous edema in hindlimbs, and paralysis of hindlimbs. Type 3 mice survived and bred normally. The mild symptoms of these mice include short but enlarged tails.

4. Treatment of Types 2 and 3 SMA-like Mice with Hydroxyurea

The effect of hydroxyurea on the symptoms of SMA-like mice were investigated. Hydroxyurea was administered to ten SMA-like mice with type 2 symptoms and ten SMA-like mice with type 3 symptoms. These mice were identified at birth by genotype and phenotype. Hydroxyurea was administered to the SMA-like mice as 1 mg/ml to 2 mg/ml solution available ad libitum in their drinking water. The amount of hydroxyurea taken by SMA-like mice was estimated to be approximate 5–10 mg/day. The survival time of hydroxyurea-treated type 2 SMA-like mice was longer, about 4 to 5 days longer on average, than untreated mice.

The effect of hydroxyurea administration on the tail phenotype of SMA-like mice was also monitored. The tails of untreated types 2 and 3 SMA-like mice have decreased diameter of muscle fibers, atrophy of muscle bundles, group atrophy and subcutaneous edema (Hsieh-Li et al. (2000) supra). After hydroxyurea treatment, the tails of most of types 2 and 3 SMA-like mice showed a nearly normal phenotype. The frequency of chronic necrosis originating at the tip of the tail was markedly reduced to 2% in hydroxyurea-treated SMA-like mice in comparison to 50% for untreated SMA-like mice. The results of western blot analysis and immunohistochemical studies demonstrated that, in hydroxyurea-treated SMA-like mice, exon 7-containing SMN protein levels were elevated in multiple tissues, including spinal cord motor neurons.

There was a very strong correlation between the function of a compound in the above-described assay of transformed lymphoid cells from SMA patients and its affect on the neurological phenotype of SMA-like diseased animals.

5. Treatment of Human SMA Patients

The effect of hydroxyurea on the symptoms of human SMA patients was examined. Hydroxyurea was used to treat two type II and one type III SMA patients who had SMN1 deletion and contain SMN2 only (J. G. Chang et al. (1995), *Am. J. Hum. Genet.* 57, 1503; J. G. Chang et al. (1997), *Hum. Genet.* 100, 577). Hydroxyurea was administered orally at a dose of 15 to 25 mg/kg/day.

The results showed that hydroxyurea elevated the full-length SMN mRNA transcript in peripheral mononuclear cells of SMA patients. Because the severity of the pathological changes in SMA patients and SMA-like mice correlated with the amount of SMN protein that contained the region encoded by exon 7, the effect of oral hydroxyurea on peripheral mononuclear cells of SMA patient is expected to be similar to the effect of spinal cord of SMA patients.

The clinical symptoms of all three patients improved. The type I patient was on respirator before treatment. She has become respirator free after hydroxyurea treatment. One of the type II patients improved to a type III phenotype. His walking gait improved after treatment. The other type II patient also demonstrated improved muscle strength.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating spinal muscular atrophy in a subject, the method comprising administering, to a human subject homozygous for mutations in SMN1, hydroxyurea in an amount sufficient to ameliorate a symptom of spinal muscular atrophy.

2. The method of claim 1, wherein the subject is a fetus, and the hydroxyurea is administered to the subject in utero.

3. The method of claim 1, wherein the symptom is muscular paralysis.

4. The method of claim 1, wherein the symptom is muscular atrophy.

5. The method of claim 1, wherein the symptom is decreased expression of full-length SMN containing exon 7 in a cell of the subject.

6. The method of claim 1, wherein the symptom is a walking gait.

7. The method of claim 1, wherein the amount is 1 to 80 mg/kg/day.

8. The method of claim 7, wherein the amount is 15 to 25 mg/kg/day.

9. The method of claim 1, wherein the amount is administered orally.

10. The method of claim 1, wherein the amount is administered by epidural injection.

11. The method of claim 1, wherein the amount is administered by parenteral injection.

* * * * *